US010745659B2

(12) United States Patent
Totani et al.

(10) Patent No.: US 10,745,659 B2
(45) Date of Patent: Aug. 18, 2020

(54) CULTURE CONTAINER AND METHOD FOR MANUFACTURING CULTURE CONTAINER

(71) Applicant: TOYO SEIKAN GROUP HOLDINGS, LTD., Tokyo (JP)

(72) Inventors: Takahiko Totani, Yokohama (JP); Satoshi Tanaka, Yokohama (JP)

(73) Assignee: TOYO SEIKAN GROUP HOLDINGS, LTD., Tokyo (JP)

( * ) Notice: Subject to any disclaimer, the term of this patent is extended or adjusted under 35 U.S.C. 154(b) by 454 days.

(21) Appl. No.: 15/627,500

(22) Filed: Jun. 20, 2017

(65) Prior Publication Data

US 2017/0283758 A1    Oct. 5, 2017

Related U.S. Application Data

(63) Continuation of application No. PCT/JP2015/005805, filed on Nov. 20, 2015.

(30) Foreign Application Priority Data

Dec. 25, 2014 (JP) ................. 2014-261643

(51) Int. Cl.
*C12M 1/12* (2006.01)
*C12M 1/00* (2006.01)
(Continued)

(52) U.S. Cl.
CPC .......... *C12M 23/14* (2013.01); *C07K 16/2803* (2013.01); *C07K 17/08* (2013.01); *C12M 25/00* (2013.01); *C12M 23/20* (2013.01)

(58) Field of Classification Search
CPC ........ C12M 23/14; C12M 23/20; C07K 17/08
See application file for complete search history.

(56) References Cited

U.S. PATENT DOCUMENTS 6,352,694 B1    3/2002 June et al.
2008/0305092 A1    12/2008 Thompson et al.
(Continued)

FOREIGN PATENT DOCUMENTS

CN    102203240 A    9/2011
CN    102433303 A    5/2012
(Continued)

OTHER PUBLICATIONS

English language machine translation of JP2007175028, accessed Sep. 16, 2019, pp. 1-23. (Year: 2019).*
(Continued)

*Primary Examiner* — William H. Beisner
(74) *Attorney, Agent, or Firm* — Osha Liang LLP

(57) ABSTRACT

A culture container for activating lymphocytes includes immobilized anti-CD3 antibodies and an anti-CD3 antibody solution including anti-CD3 antibodies, wherein the culture container is formed in a bag-like shape and is formed of a soft-packaging material, the immobilized anti-CD3 antibodies are immobilized at a density of 10 to 300 ng/cm$^2$ on one surface of opposing inner surfaces within the container, and the anti-CD3 antibody solution is enclosed in the container in an amount of 0.25 to 400 ng of the anti-CD3 antibodies in 0.1 to 800 µl of the solution per 1 cm$^2$ of a culture surface formed of the one surface.

5 Claims, 2 Drawing Sheets

(51) Int. Cl.
*C07K 16/28* (2006.01)
*C07K 17/08* (2006.01)

(56) References Cited

U.S. PATENT DOCUMENTS

2011/0318828 A1 12/2011 Suzuki et al.
2014/0127805 A1 5/2014 Suzuki et al.

FOREIGN PATENT DOCUMENTS

| JP | 2007-056034 A | 3/2007 |
| JP | 2007175028 A | 7/2007 |
| JP | 2010-099022 A | 5/2010 |
| JP | 2012239401 A | 12/2012 |
| WO | 93-19767 A1 | 10/1993 |

OTHER PUBLICATIONS

Yixin Li et al: "Comparison of anti-CD3 and anti-CD28-coated-beads with soluble anti-CD3 for expanding human T cells: Differing impact on CD8 T cell phenotype and responsiveness to restimulation," Journal of Translational Medicine, Biomed Central, vol. 8, No. 1, Oct. 26, 2010 (15 pages).

Extended European Search Report issued in European application No. 15872148.0; dated Aug. 2, 2018 (8 pages).
Office Action issued in corresponding Chinese Application No. 201580067308.0; dated Sep. 19, 2018 (10 pages).
International Search Report and Written Opinion dated Feb. 16, 2016, by the Japan Patent Office in corresponding International Application No. PCT/JP2015/005805, with English translation (9 pages).
PCT International Preliminary Report on Patentability (IPRP) and Written Opinion dated Jun. 27, 2017, by the International Bureau of WIPO in corresponding International Application No. PCT/JP2015/005805, with English translation (12 pages).
Ochoa, Augusto C., et al., "Lymphokine-activated Killer Activity in Long-Term Cultures with Anti-CD3 plus Interleukin 2: Identification and Isolation of Effector Subsets"; American Association for Cancer Research (downloaded from cancerres.aacrjournals.org, Feb. 3, 2016]; Cancer Research, vol. 49, 1989; pp. 963-968 (7 pages).
Fujino, Michio, et al., "Effect of Anti-CD3 Antibody (OKT3) on the cytotoxicity of LAK Cells Induced from Regional Lymph Node Lymphocytes in Lung Cancer Patients"; Japanese Journal of Lung Cancer, vol. 35, No. 3, 1995; pp. 253-261.
Sekine, T., et al., "A feasible method for expansion of peripheral blood lymphocytes by culture with immobilized anti-CD3 monoclonal antibody and interleukin-2 for use in adoptive immunotherapy of cancer patients"; Biomed & Pharmacotherapy, vol. 47, 1993; pp. 73-78.

* cited by examiner

CULTURE CONTAINER AND METHOD FOR MANUFACTURING CULTURE CONTAINER

TECHNICAL FIELD

One or more embodiments of the present invention relate to a technology of culturing cells, and more particularly, one or more embodiments of the present invention relate to a culture container for activating lymphocytes and a method for producing the same.

BACKGROUND

In recent years, in the field of production of medicine, gene therapy, regenerative medicine, immunotherapy etc., it is required to culture efficiently a large amount of cells, tissues, microorganisms etc. in an artificial environment.

Under such circumstances, a large amount of cells are cultured automatically in a closed system by enclosing cells and a culture medium in a culture container formed of a gas-permeable film.

In particular, when culturing lymphocytes, it is necessary to conduct culture aiming at activating lymphocytes by using anti-CD3 antibodies prior to culturing in order to increase the number of cells. Therefore, by admitting lymphocytes and a culture medium into a culture container in which anti-CD3 antibodies are contained, activation of lymphocytes is conducted.

Meanwhile, when only a small amount of anti-CD3 antibodies in the form of a solution is present in a culture container, stimulation to lymphocytes becomes insufficient and activation cannot be conducted sufficiently. On the other hand, when a large amount of anti-CD3 antibodies in the form of a solution is present in a culture container, CD3 antigens present in cell membranes are removed from by the defense mechanism of cells, whereby activation of lymphocytes is inhibited.

Immunosuppressive agents containing anti-CD3 antibodies as a main component were produced as a result of attention paid to such properties of lymphocytes, and when they are administered to patients who had rejection after organ/tissue transplantation, a large amount of anti-CD3 antibodies are bound to antigens and then accumulated, and the accumulated product is taken in the cells and discharged outside the cells. Alternatively, the accumulated product is cleaved by enzymes and antigens are removed from the cell surface. As a result, the stimulation is no longer transmitted to the inside of the cell, and the activation of lymphocytes is suppressed.

As mentioned above, it is difficult to appropriately control the activation of lymphocytes by using antibodies liberated in a solution. Conventionally, in general,—anti-CD3 antibodies are immobilized on the inner surface of the bottom of a culture container, and appropriate stimulation apply to lymphocytes by using such a culture container, thereby activation of lymphocytes has been widely conducted.

When producing a culture bag for activation of lymphocytes (hereinafter, often simply referred to as the "activation bag"), after enclosing an antibody solution containing anti-CD3 antibodies in a bag and immobilizing the anti-CD3 antibodies on the inner surface of the bag, the inside of the bag is washed to remove liberated antibodies, and thereafter, lymphocytes and a culture medium are enclosed to conduct culture for activation. By washing the inside of the bag to remove liberated antibodies, it was possible to activate lymphocytes more efficiently.

Patent Document 1: JP-A-2007-17502B

Under such circumstances, in order to examine adverse effects exerted on activation by liberated antibodies when an antibody solution remains in an activation bag, the inventors conducted activation of lymphocytes by using antibody solutions at various concentrations.

As a result, it has been found the following. When the concentration of antibodies is relatively high, i.e. as high as that used for production of an activation bag, activation of lymphocytes is suppressed. However, surprisingly, when the concentration of antibodies is low in a certain range, activation of lymphocytes is promoted.

That is, it has been revealed that, by immobilizing anti-CD3 antibodies in a bag for activation and by enclosing a low-concentration liberated antibody, it becomes possible to promote activation of lymphocytes by the activation bag, and as a result, proliferation efficiency of lymphocytes can be further improved.

Here, in Example 1 of the Patent Document 1, after an antibody solution containing anti-CD3 antibodies is enclosed within a bag and the anti-CD3 antibodies are immobilized on the inner surface of the bag, activation is conducted with the antibody solution being enclosed in order to produce an activation bag for lymphocytes. Further, in Example 2 of the Patent Document 1, after immobilizing anti-CD3 antibodies on the inner surface of the bag, the bag is washed to remove liberated antibodies, and then lymphocytes and a culture medium are enclosed to conduct activation. Patent Document 1 also states that in Example 1 in which activation is conducted with the antibody solution being enclosed, proliferation efficiency of lymphocytes was lower as compared with Example 2 in which liberated antibodies were removed by washing the inside of the bag.

That is, it is thought that, in Example 1, activation of lymphocytes was suppressed since a large amount of liberated antibodies were remained in the bag, and hence, proliferation efficiency of lymphocytes was lower than that in Example 2.

On the other hand, Patent Document 1 neither describe nor suggest that liberated antibodies in a certain low concentration range are enclosed in an activation bag in which anti-CD3 antibodies are immobilized.

SUMMARY

One or more embodiments of the present invention provide a culture container capable of activating lymphocytes at a higher efficiency than that attained by conventional containers and the method for producing the same.

The culture container according to one or more embodiments of the present invention is a culture container for activating lymphocytes that is formed in a bag-like shape and is formed of a soft-packaging material, wherein, anti-CD3 antibodies are immobilized at a density of 10 to 300 NG/cm$^2$ on one surface of opposing inner surfaces within the container, and anti-CD3 antibodies in the form of a solution are enclosed in an amount of 0.25 to 400 ng and 0.1 to 800 µl per 1 cm$^2$ of a culture surface formed of said one surface.

The method for producing a culture container according to one or more embodiments of the present invention is a method for producing a culture container for activating lymphocytes that is formed in a bag-like shape and is formed of a soft-packaging material, comprising:

immobilizing anti-CD3 antibodies on one surface of opposing inner surfaces within the container at a density of 10 to 300 ng/cm$^2$, and enclosing anti-CD3 antibodies in the form of a solution in an amount of 0.25 to 400 ng and 0.1 to 800 μl per 1 cm² of a culture surface formed of the one surface.

According to one or more embodiments of the present invention, it is possible to provide a culture container capable of activating lymphocytes at an efficiency higher than that of conventional container and the method for producing the same.

DETAILED DESCRIPTION OF THE EMBODIMENTS

Figure 1:
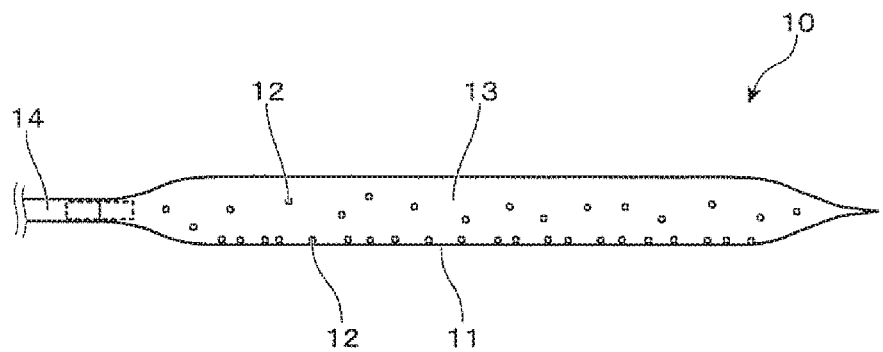
FIG. 1 is a schematic front view showing an outline of the culture container according to one or more embodiments of the present invention.
Figure 2:
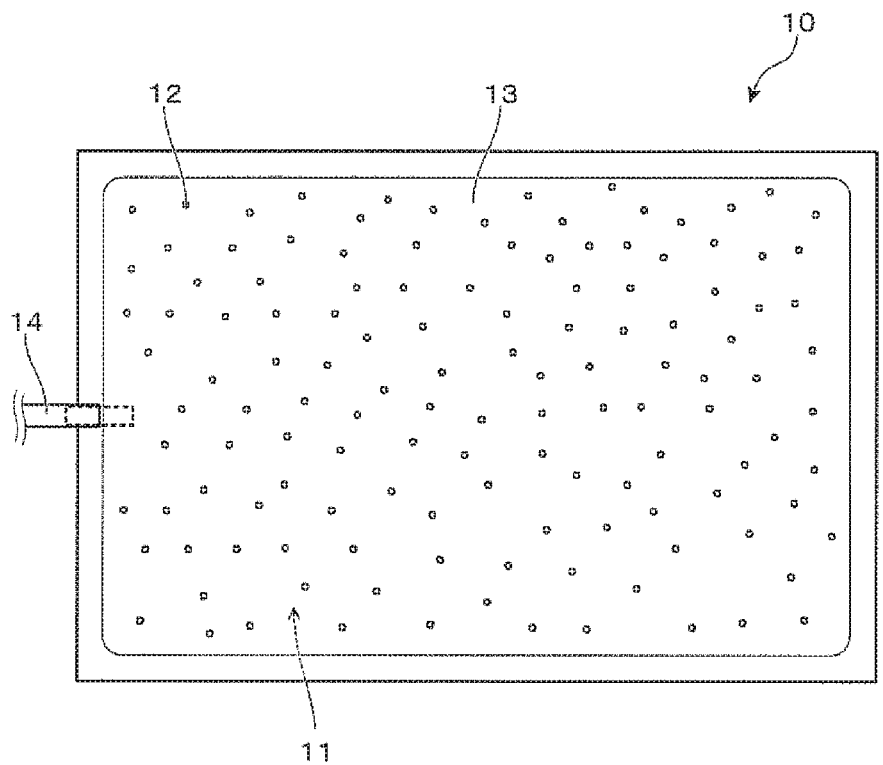
FIG. 2 is a schematic plan view showing an outline of the culture container according to one or more embodiments of the present invention.
Figure 3:
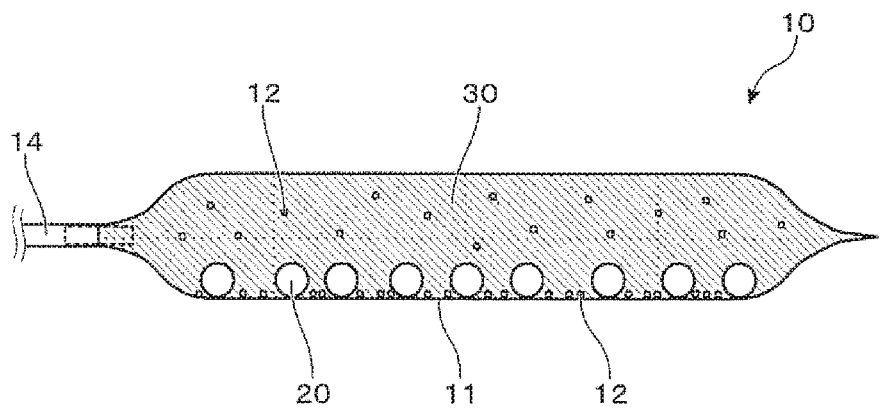
FIG. 3 is a schematic front view showing a manner in which lymphocytes and a culture medium are enclosed in the culture container according to one or more embodiments of the present invention to conduct culture for activation.
Figure 4:
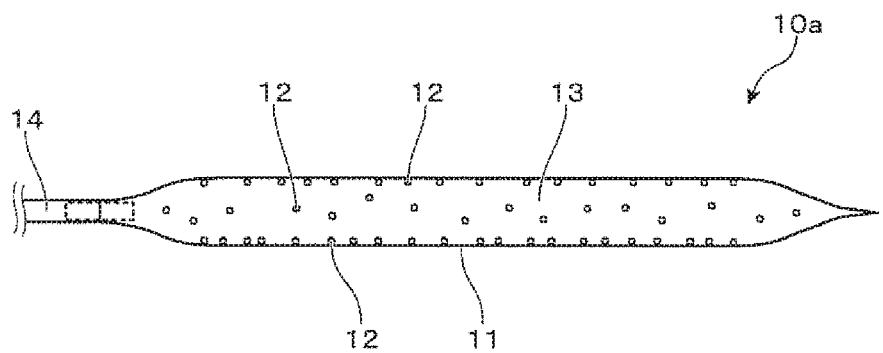
FIG. 4 is a schematic front view showing an outline of an application example of the culture container according to one or more embodiments of the present invention.

Hereinbelow, as for one or more embodiments of the present invention of the culture container and the method for producing a culture container, a detailed explanation will be made with reference to FIGS. 1 to 4. FIG. 1 is a schematic front view showing an outline of the culture container according to one or more embodiments of the present invention, FIG. 2 is a schematic plan view showing an outline of the culture container according to one or more embodiments of the present invention, and FIG. 3 is a schematic front view showing a manner in which lymphocytes and a culture medium are enclosed in the culture container according to one or more embodiments of the present invention to conduct culture for activation. FIG. 4 is a schematic front view showing an outline of the application example of the culture container according to one or more embodiments of the present invention.

[Culture Container]

As shown in FIGS. 1 and 2, the culture container 10 according to one or more embodiments of the present invention has container walls opposing to each other vertically. One of the inner surfaces of the container (bottom surface within the container in FIGS. 1 and 2) serves as an immobilized surface 11 on which antibodies 12 are immobilized. This immobilized surface 11 is used as a culture surface. Within the culture container 10, an antibody solution 13 in which the antibodies 12 are liberated is enclosed.

In the culture container 10, a port that can connect the tube 14 is provided. Through this port, enclosing of lymphocytes and a culture medium into the culture container 10 and collection of cultured lymphocytes and a culture medium are conducted. In the examples shown in FIGS. 1 and 2, one of the tubes 14 is connected to the culture container 10, but two or more tubes may be connected.

The culture container 10 is formed in a bag-like shape by using a film having permeability to gasses that is required for cell culture. As the material for such culture container 10, a polyolefin-based resin such as polyethylene and polypropylene may be used.

As the antibodies 12 that are immobilized on the immobilized surface 11, anti-CD3 antibodies are used. Lymphocytes can be activated by anti-CD3 antibodies and proliferated.

The density of the antibodies 12 immobilized on the immobilized surface 11 may be 10 to 300 ng/cm², or 10 to 40 ng/cm².

By allowing the density of the immobilized antibodies 12 to be 10 ng/cm² or more, it is possible to activate lymphocytes effectively. Further, since the closest packing density of the anti-CD3 antibodies in the immobilized surface 11 is 300 ng/cm², by immobilizing the antibodies 12 up to this density range, lymphocytes can be activated. Furthermore, by allowing the density of the antibodies 12 immobilized to be 10 to 40 ng/cm², it is possible to increase proliferation efficiency of lymphocytes particularly significantly.

In the culture container 10, in the immobilized surface 11 used as a culture surface, the antibodies 12 in the form of a solution may be enclosed in an amount of 0.25 to 400 ng and 0.1 to 800 μl per 1 cm² of the surface. The reason therefor is that, by enclosed the antibodies 12 in the form of a solution in the culture container 10 in such an amount, activation of lymphocytes can be further promoted, and as a result, proliferation efficiency can be further improved.

In this respect, the antibodies 12 in the form of a solution may be enclosed, per 1 cm² of the culture surface, in an amount of 0.5 to 300 ng and 0.1 to 600 μl, in an amount of 1 to 200 ng and 0.1 to 400 μl, or in an amount of 1 to 200 ng and 0.1 to 200 μl.

The concentration of liberated anti-CD3 antibodies in the culture container 10 (hereinafter often referred to as a liberated antibody concentration) may be 5 to 100 ng/ml. By allowing the liberated antibody concentration to be within such a range, it is possible to activate lymphocytes more effectively, and as a result, cell proliferation efficiency can be further improved.

Here, in order to obtain an excellent culture efficiency, cell culture conducted by using a culture container formed of a soft packaging material is generally conducted with the liquid thickness of a culture medium being 0.2 to 2 cm often. When the liberated antibody concentration is 5 ng/ml, if the liquid thickness of a culture medium is 0.2 cm, the amount of antibodies per 1 cm² is 1 ng. Further, when the liberated antibody concentration is 100 ng/ml, if the liquid thickness of a culture medium is 2 cm, the amount of antibodies per 1 cm² is 200 ng. Therefore, when the liberated antibody concentration is 5 to 100 ng/ml and the liquid thickness of the culture medium is 0.2 to 2 cm, the antibodies 12 in the form of a solution be enclosed in the culture container 10 in an amount of 1 to 200 ng per 1 cm² of the culture surface.

Further, there may be a case where the liquid thickness of the culture medium is selected from a range of 0.05 to 4 cm for the reason of necessity of adjusting the cell density, etc. In such case, when culture is conducted with a liberated antibody concentration is 5 to 100 ng/ml, in the case of the liberated antibody concentration is 5 ng/ml, the amount of antibodies per 1 cm² is 0.25 ng in the case of the liquid thickness is 0.05 cm. Further, if the liberated antibody concentration is 100 ng/ml, the amount of antibodies per 1 $cm^2$ is 400 ng in the case of the liquid thickness is 4 cm. Therefore, the antibodies 12 in the form of a solution are enclosed in the culture container 10 in an amount of 0.25 to 400 ng per 1 $cm^2$ of the culture surface.

Further, since it is difficult to enclose anti-CD3 antibodies in the form of a solution in a culture container in an amount smaller than 0.1 μl per 1 $cm^2$ of the culture surface, anti-CD3 antibodies in the form of a solution may be enclosed in an amount of 0.1 μl or more. Further, in respect of such as handling of a culture container formed of a soft packaging material, the capacity of a commonly used culture container is in many cases 4000 μl or less per 1 $cm^2$ of the culture surface. The ratio of the antibody solution relative to the amount of a culture medium may be 20% or less, 10% or less or 5% or less in order to obtain an excellent culture efficiency. Therefore, anti-CD3 antibodies in the form of e solution may be enclosed in the culture container in an amount of 800 μl or less, in an amount of 400 μl or less, or 200 μl or less per 1 $cm^2$ of the culture surface.

By conducting activation of lymphocytes by admitting lymphocytes and a culture medium into such a culture container 10 through the tube 14, as compared with a case where a culture container in which only the antibodies 12 are immobilized is used, it is possible to allow lymphocytes to be in contact with anti-CD3 antibodies, whereby activation efficiency of lymphocytes can be further improved.

FIG. 3 schematically shows the manner of such culture for activation. Not only the antibodies 12 are immobilized on the inner bottom surface of the culture container 10, but also the antibodies 12 are liberated at a low concentration in the culture medium 30. As a result, the lymphocytes 20 are activated by immobilized antibodies 12 and liberated antibodies 12.

Further, the culture container according to one or more embodiments of the present invention may be configured as a culture container 10a in which anti-CD3 antibodies are immobilized on the inner surface of the container that is opposed to the immobilized surface 11 (hereinafter often referred to as the "opposing surface") at lower density than the density of the immobilized surface 11, as shown in FIG. 4.

That is, when the opposing surface is a non-immobilized surface on which antibodies 12 are not immobilized, if liberated antibodies are adsorbed on the non-immobilized surface, for example, during storage or transportation, concentration of liberated antibodies is lowered, and as a result, control of concentration thereof becomes difficult.

Accordingly, in the culture container 10a in this embodiment, by immobilizing anti-CD3 antibodies on the opposing surface, it becomes possible to suppress lowering of the concentration of liberated antibodies in the culture container. The concentration of anti-CD3 antibodies to be immobilized on the opposing surface is not particularly restricted, but the concentration may be about 0.01 to 0.9 times as large as the concentration of anti-CD3 antibodies on the immobilized surface 11.

[Method for Producing Culture Container]

The culture container 10 according to one or more embodiments of the present invention can be produced as follows, for example.

First, low-density polyethylene is molded by extrusion by using a plastic extrusion molding apparatus, thereby to form a film. Then, by using an impulse sealer, a bag-shaped culture container 10 is produced from this film. Further, the tube 14 is connected to the culture container 10 through a port.

Subsequently, the culture container 10 is mounted on a mounting table, and a prescribed amount of a gas is enclosed. A buffer solution in which the antibodies 12 are dissolved is subsequently enclosed. By such as swinging the culture container 10, droplets of the buffer solution are moved on the bottom surface within the culture container 10, whereby the antibodies 12 contained in the buffer solution are adhered to the bottom surface within the culture container 10.

At this time, anti-CD3 antibodies are used as the antibodies 12 to be immobilized on the immobilizing surface 11, and as mentioned above, the density of the antibodies 12 to be immobilized on the immobilizing surface 11 may be 10 to 300 $ng/cm^2$, or 10 to 40 $ng/cm^2$.

Also, by immobilizing anti-CD3 antibodies on the container inner surface opposing to the immobilizing surface 11, the culture container 10a shown in FIG. 4 can be produced.

At this time, anti-CD3 antibodies may be immobilized at a density of about 0.01 to 0.9 times of that of the immobilizing surface 11.

Further, anti-CD3 antibodies in the form of a solution are enclosed in the culture container 10 (or culture container 10a) immobilized the antibodies 12 in this way in an amount of 0.25 to 400 ng and 0.1 to 800 μl per 1 $cm^2$ of the culture surface (immobilizing surface 11). As mentioned above, anti-CD3 antibodies in the form of a solution may be enclosed, per 1 $cm^2$ of the culture surface, in an amount of 0.5 to 300 ng and 0.1 to 600 μl, or in an amount of 1 to 200 ng and 0.1 to 400 μl, or in an amount of 1 to 200 ng and 0.1 to 200 μl.

As explained above, according to one or more embodiments of the present invention, it is possible to obtain a culture container in which, not only the immobilized surface 11 in which the antibodies 12 are immobilized, but also anti-CD3 antibodies in the form of a solution are enclosed in the optimum amount mentioned above can be obtained. By using this culture container, it is possible to activate lymphocytes more efficiently than a conventional one, and as a result, it is possible to improve proliferation efficiency of lymphocytes furthermore efficiently.

EXAMPLES

Activation of lymphocytes was conducted by producing culture containers in which antibody solutions with various concentrations were enclosed, and proliferation efficiency of lymphocytes in each culture container was confirmed. Specifically, the following was conducted.

Experiment 1

[Production of Culture Container]

Low-density polyethylene was extruded using Labo Plastomill (manufactured by Toyo Seiki Seisaku-sho, Ltd) to form a film having a thickness of 100 μm. Then, a bag of 11 cm×20.5 cm (about 225 $cm^2$) was prepared with an impulse sealer.

[Immobilization of Antibodies]

About 250 ml of air was enclosed in this bag, and 2 ml of antibody solution which is composed a phosphate buffer solution (by Life Technologies Japan Ltd.) dissolved 20 μg of anti-CD3 antibodies (manufactured by TAKARA BIO INC.) was enclosed. Then, the bag was swung so that the droplets were moved on the inner surface of the bag at a speed of 10 m/min for 2.5 minutes. Subsequently, after discharging the antibody solution, the bag was washed by enclosing 2 ml of a phosphate buffer solution, moving the solution on the inner surface of the bag at a speed of 10 m/min for 2.5 minutes and discharging, whereby liberated antibodies were removed from the inner of the bag. As a result of measurement of the amount of immobilized antibodies by the BOA method, the amount of immobilized antibodies was 37 ng/cm$^2$.

[Production of Bag for Activation Culture Test]

The bag in which antibodies were immobilized was re-sized into 5 cm×5 cm by using the impulse sealer and a bag for using an activation culture test was prepared. Subsequently, 50 µl of a phosphate buffer solution in which anti-CD3 antibodies were dissolved (1 µg/ml, 5 µg/ml, 10 µg/ml, 20 µg/ml and 50 µg/ml, respectively) such that the concentrations of liberated antibodies at the time of culturing became 10 ng/ml, 50 ng/ml, 100 ng/ml, 200 ng/ml and 500 ng/ml, respectively, was enclosed in the bag for activation test. As a control, a bag in which a phosphate buffer solution in which anti-CD3 antibodies were dissolved was not enclosed was prepared.

[Step of Activating Lymphocytes]

8.2×10$^5$ of human peripheral blood mononuclear cells (manufactured by Cell Applications, Inc.) as one of lymphocytes were suspended in an ALyS505N-7 medium (manufactured by Cell Science & Technology Institute, Inc.) containing 2% fetal bovine serum (manufactured by Life Technologies Japan Ltd.), whereby a cell suspension liquid was prepared. Then, 5 ml of the cell suspension liquid was enclosed in each of the bags for activation culture test.

By allowing these bags to conduct stationary culture at 37° C. for 116 hours, activation of lymphocytes was conducted (activation culture step). Then, the number of cells in the bags was counted at the time of completing the activation culture, and the proliferation ratios were calculated. The results are shown in FIG. 5.

Figure 5:
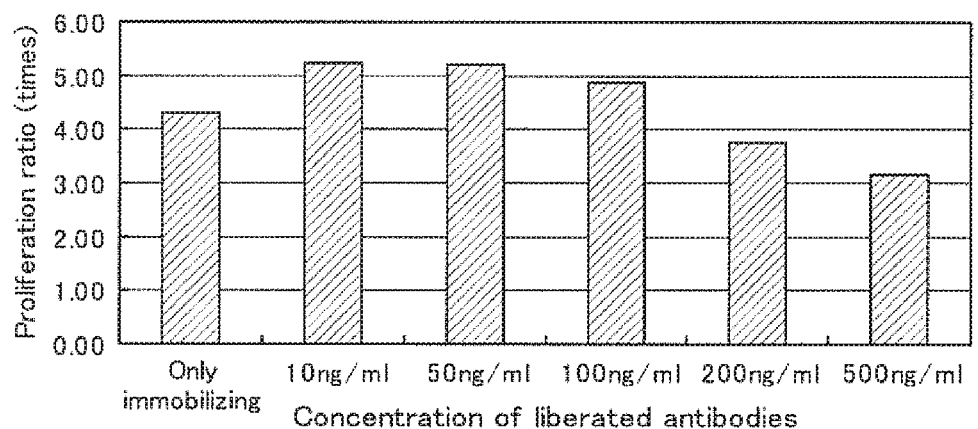
FIG. 5 is a view showing the results of Experiment 1 (only a step of culture for activation) demonstrating cell proliferation ratios at various liberated antibody concentrations (10 ng/ml to 500 ng/ml) of the culture container according to one or more embodiments of the present invention.

As shown in FIG. 5, the proliferation ratio of lymphocytes was 4.30 times in the control experiment (only immobilizing), 5.24 times when the liberated antibody concentration was 10 ng/ml, 5.20 times when the liberated antibody concentration was 50 ng/ml, 4.88 times when the liberated antibody concentration was 100 ng/ml, 3.77 times when the liberated antibody concentration was 200 ng/ml and 3.18 times when the a liberated antibody concentration was 500 ng/ml.

That is, it can be understood that, when the liberated antibody concentration is 10 ng/ml to 100 ng/ml, proliferation efficiency of antibodies was improved as compared with a case where activation was conducted only by immobilized antibodies.

On the other hand, when the liberated antibody concentration was 200 ng/ml or more, proliferation efficiency of antibodies was lowered as compared with a case where activation was conducted only by immobilized antibodies.

As indicated above, when the liberated antibody concentration was in the certain low concentration range as above, the proliferation efficiency of lymphocytes can be further improved. On the other hand, when the liberated antibody concentration—was large, it is thought that activation of lymphocytes was inhibited, whereby proliferation efficiency was lowered.

Experiment 2

An experiment was conducted in order to examine the proliferation efficiency of lymphocytes when the liberated antibody concentration in the culture container was smaller than 10 ng/ml. Production of a culture container and immobilization of antibodies were conducted in the same manner as in Experiment 1.

[Preparation of Bag for Activation Culture Test]

The bag in which antibodies were immobilized was re-sized into 5 cm×5 cm by using the impulse sealer and a bag for using in an activation culture test was prepared. Subsequently, 50 µl of a phosphate buffer solution in which anti-CD3 antibodies were dissolved (0.5 µg/ml, 1 µg/ml, respectively) such that the concentrations of liberated antibodies at the time of culturing became 5 ng/ml and 10 ng/ml, respectively, was enclosed in the bag for activation test. As a control, a bag in which a phosphate buffer solution in which anti-CD3 antibodies were dissolved was not enclosed was prepared.

[Step of Activating Lymphocytes]

8.6×10$^5$ of human peripheral blood mononuclear cells (manufactured by Cell Applications, Inc.) as one of lymphocytes were suspended in an ALyS505N-7 medium (manufactured by Cell Science & Technology Institute, inc.) containing 2% fetal bovine serum (manufactured by Life Technologies Japan Ltd.), whereby a cell suspension liquid was prepared. Then, 5 ml of the cell suspension liquid was enclosed in each of the bags for activation culture test.

By allowing these bags to conduct stationary culture at 37° C. for 122 hours, activation of lymphocytes was conducted.

Subsequently, activated lymphocytes were transferred to dishes on which no antibodies were immobilized (manufactured by Corning Incorporated), and cultured for 192 hours while appropriately diluting (amplification culture step). Then, the number of cells in the bags was counted at the time of completing the amplification culture, and proliferation ratios were calculated. The results are shown in FIG. 6.

Figure 6:
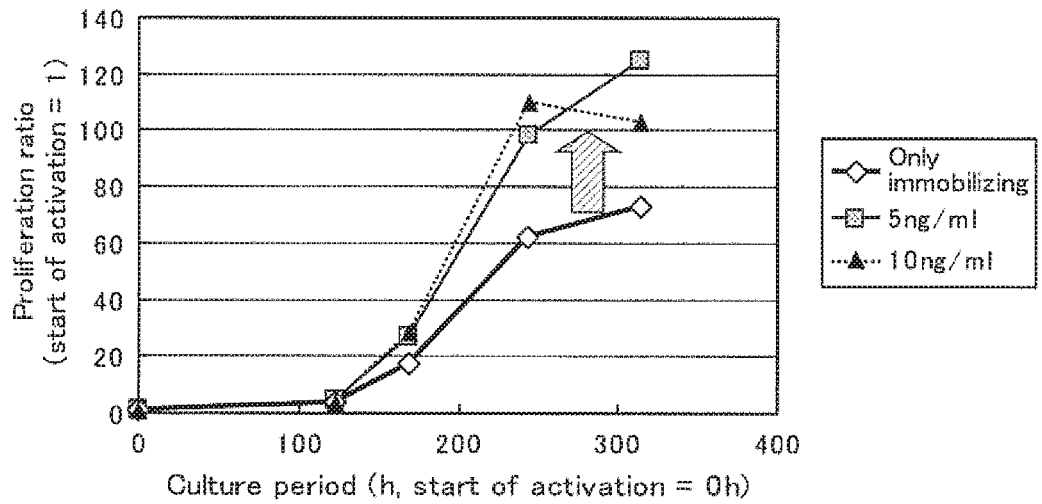
FIG. 6 is a view showing the results of Experiment 2 (a step of culture for activation+a step of amplification culture) demonstrating the cell proliferation ratios at various liberated antibody concentrations (5 ng/ml, 10 ng/ml) of the culture container according to one or more embodiments of the present invention.

As shown in FIG. 6, the proliferation ratio of lymphocytes was 73 times in the control experiment (only immobilizing), 125 times when the liberated antibody concentration was 5 ng/ml, and 103 times when the liberated antibody concentration—was 10 ng/ml.

That is, it was revealed that, when the liberated antibody concentration-were 5 ng/ml and 10 ng/ml, proliferation efficiency was greatly increased as compared with a case where activation was conducted with only immobilized antibodies.

As indicated above, by the results of Experiment 1 and Experiment 2, it was confirmed that, when the liberated antibody concentration was 5 to 100 ng/ml, the proliferation efficiency could be improved as compared with a case where activation was conducted with only immobilized antibodies.

The present invention is not limited to the above-mentioned embodiments or examples, and it is needless to say that various modifications are possible within the scope of the present invention.

For example, appropriate modifications are possible; i.e., using a culture container having a size different from that the culture container in the Examples, using lymphocytes different from those used in the Examples, using a different type of a culture medium, etc.

The present invention may be used when a large amount of lymphocytes is cultured.

The documents described in the specification and the specification of Japanese application(s) on the basis of which the present application claims Paris convention priority are incorporated herein by reference in its entirety. Although the disclosure has been described with respect to only a limited number of embodiments, those skilled in the art, having benefit of this disclosure, will appreciate that various other embodiments may be devised without departing from the scope of the present invention. Accordingly, the scope of the invention should be limited only by the attached claims.

EXPLANATION OF REFERENTIAL NUMERALS 10, 10a Culture container
11 Immobilized surface
12 Antibodies
13 Antibody solution
14 Tube
20 Lymphocytes
30 Culture medium

The invention claimed is:

1. A culture container for activating lymphocytes, comprising:
   immobilized anti-CD3 antibodies and an anti-CD3 antibody solution comprising anti-CD3 antibodies, wherein:
   the culture container is formed in a bag shape and is formed of a soft-packaging material,
   the immobilized anti-CD3 antibodies are immobilized at a density of 10 to 300 ng/cm$^2$ on one surface of opposing inner surfaces within the container, and
   a concentration of the anti-CD3 antibodies liberated in the culture container is 5 to 100 ng/ml.

2. The culture container according to claim 1, wherein the immobilized anti-CD3 antibodies are immobilized on an inner surface within the container opposing to the culture surface at a density smaller than the density at the culture surface.

3. The culture container according to claim 1, wherein the immobilized anti-CD3 antibodies are immobilized at a density of 10 to 40 ng/cm$^2$ on the one surface of opposing inner surfaces within the container.

4. A method for producing a culture container for activating lymphocytes, wherein the culture container is formed in a bag shape and is formed of a soft-packaging material, the method comprising:
   immobilizing anti-CD3 antibodies on one surface of opposing inner surfaces within the container at a density of 10 to 300 ng/cm$^2$, and
   enclosing in the container an anti-CD3 antibody solution comprising anti-CD3 antibodies, wherein a concentration of the anti-CD3 antibodies liberated in the culture container is 5 to 100 ng/ml.

5. The method for producing a culture container according to claim 4 wherein the anti-CD3 antibodies are immobilized at a density of 10 to 40 ng/cm$^2$ on the one surface of opposing inner surfaces within the container.

* * * * *